(12) United States Patent
McMichael et al.

(10) Patent No.: US 6,187,309 B1
(45) Date of Patent: Feb. 13, 2001

(54) METHOD FOR TREATMENT OF SYMPTOMS OF CENTRAL NERVOUS SYSTEM DISORDERS

(75) Inventors: John McMichael, Delanson, NY (US); Allan D. Lieberman, Charleston, SC (US)

(73) Assignee: Milkaus Laboratory, Inc., Delanson, NY (US)

( * ) Notice: Under 35 U.S.C. 154(b), the term of this patent shall be extended for 0 days.

(21) Appl. No.: 09/514,993

(22) Filed: Feb. 29, 2000

Related U.S. Application Data

(60) Provisional application No. 60/153,838, filed on Sep. 14, 1999.

(51) Int. Cl.[7] .................................................... A61K 39/42
(52) U.S. Cl. ............................................................ 424/159.1
(58) Field of Search ............................................ 424/159.1

(56) References Cited

U.S. PATENT DOCUMENTS

| 4,384,993 | * | 5/1983 | Sato et al. ........................ 260/112 B |
| 4,692,331 | * | 9/1987 | Uemaura et al. ...................... 424/85 |

* cited by examiner

*Primary Examiner*—Raymond Henley, III
(74) *Attorney, Agent, or Firm*—Marshall, O'Toole, Gerstein, Murray & Borun

(57) ABSTRACT

The present invention provides a method for treating the symptoms of autism comprising the step of administering an effective amount of anti-rubeola antibody.

22 Claims, No Drawings

METHOD FOR TREATMENT OF SYMPTOMS OF CENTRAL NERVOUS SYSTEM DISORDERS

This application claims priority from U.S. Provisional Application Ser. No. 60/153,838 filed Sep. 14, 1999.

BACKGROUND OF THE INVENTION

The present invention relates generally to autism and specifically to a method for treatment of the symptoms of central nervous system disorders including autism, multiple sclerosis (MS) and attention deficit disorder/attention deficit as hyperactivity disorder (ADD/ADHD).

Autism is a profound and poorly understood developmental disorder that severely impairs a person's abilities, particularly in the areas of language and social relations. The disabilities of autistic children in language and communication range from mild to profound. In many cases the disorder is evident during the first 30 months of life. Autistic children are normal in appearance, physically well developed and are usually boys (by a ratio of 3:1).

The most distinctive feature of autistic children is that they appear isolated from the world around them and may appear detached, aloof, or in a dreamlike world. Autistic children often appear only vaguely aware of others in their environment, including family members, and frequently display unusual mannerisms and engage in ritualistic behavior. Appropriate play with other children or toys is uncommon and there is often a great interest in inanimate objects, especially mechanical devices and appliances. Historically, children were frequently institutionalized by the ages of nine or ten because their parents were no longer able to control them. While, the availability and effectiveness of behavioral support services and advances in treatment and education of treatment of children with autism have reversed the trend toward institutionalization autistic children still require significant resources for their care.

There are no medical tests that can be used to determine autism. Instead, the diagnosis of autism is made when a subject displays six of 12 characteristic behaviors that match the criteria in the Diagnostic and Statistical Manual, Fourth Edition (DSM IV), published by the American Psychiatric Association. Subjects with autism, compared to other disabled persons of commensurate ability, are more difficult to teach and comparatively have significantly greater problems acquiring and using language and relating socially. Historically, about 75 percent of subjects with autism are classified as mentally retarded.

Autism was first described by Dr. Leo Kanner, a psychiatrist at John Hopkins University in the 1940's who examined a group of 11 children who were self-absorbed and who had severe social, communication, and behavioral problems. It was originally believed that subjects with autism had good cognitive potentialities and that autistic children possessed latent genius that could be unlocked by discovery of the appropriate key for that child. Associated with that belief was the misconception that autism was caused by parent's behavior and particularly was the result of "cold" mothers whose projection of hopelessness, despair and apathy was projected onto their children.

More recently, this psychoanalytic view of autism was replaced by a neurologically based approach and continuing study as to the organic causes of the disease. Of interest to the present invention is the observation that the incidence of autism may be increasing in the population in the United States and other developed countries. In a recent report to the state legislature, the California Department of Developmental Services has described a three-fold increase in the number of persons with autism statewide between 1987 and 1998 and a doubling of the percentage of total mental health client population accounted for by persons with autism during that time. Similar observations have been made elsewhere in the United States and in other developed countries.

Much speculation concerning the apparent increase in the incidence of autism has focused on possible links between immunological causes of the disease. Prenatal and postnatal infections have been implicated as possible causes of autism. In particular, congenital rubella and HSV infections have been associated with incidence of autism.

Links between a family history of autoimmune disorders such as type 1 diabetes, adult rheumatoid arthritis, hypothyroidism and systemic lupus erythematosus have also been observed with the occurrence of autism suggesting that immune dysfunction may interact with various environmental factors to play a role in autism pathogenesis. Journal of Child Neurology, vol. 14, number 6 pp. 388–394 (June 1999).

Other workers have reported an association between autism and the presence of antibodies against human herpes virus-6, as well as autoantibodies against tissues of the central nervous system such as myelin basic protein (MBP). See Warren et al. Neuropsycholobiology 34:72–75 (1996).

In addition, Asperger, "Die Pyschopathologie des coeliakakranken kindes." Ann, Paediatr 197: 146–151 (1961) reported an association between intestinal dysfunction and autism. Other studies including those of Walker-Smith et al. Lancet ii: 883–84 (1972) and D'Eufemia Acta Paediatrica 85: 1076–79 (1996) which show low concentrations of alpha-1 antitrypsin and abnormal intestinal permeability respectively suggest that the consequences of an inflamed or dysfunctional intestine may play a part in behavioral changes in some patients.

Recently, attention has focused on the possibility of an association between childhood vaccinations and autism. Both, infection and the immune reaction resulting from immunization would be consistent with an immunological cause of the disease. In particular, the combined measles, mumps, and rubella (MMR) vaccine, rather than the monovalent measles vaccine, has been associated with the onset of autism. See Gupta Proc. Natl. Autism Assn. Chicago 1996, 455–460. This observation has led to the suggestion that some form of immune overload may constitute an aspect of susceptibility to measles vaccination. As a consequence, some workers in the field have suggested a suspension of administration of the combined MMR vaccine in favor of sequential administration over time of the three vaccine components.

Wakefield et al. Lancet 351: 637–641 (1998) identified a chronic enterocolitis in children related to neuropsychiatric dysfunction and autism. In most cases, the onset of symptoms occurred after immunization with the MMR vaccine. While Wakefield et al. stated that they had not proven an association between MMR vaccine and the syndrome described they suggested that ongoing virological and epidemiological studies might resolve the issue. At that time, Wakefield et al. suggested that the published evidence was inadequate to show whether there was a change in incidence or a link with MMR vaccine. But see, Peltola, et al. Lancet 351:1327–1328 (1998) which reported work in which children who received the MMR vaccination in Finland between 1982 and 1996 were traced but failed to find support for the suggestion that the vaccination could cause autism or bowel disease. Additional work by Wakefield and others indicates that there exists live measles (rubeola) vaccine virus in the guts of the vast majority of autistic children and that autistic patients often have a serum antibody titer to rubeola virus hundreds of times higher than normal, suggesting continual or oft-repeated exposure and/or incomplete or failed elimination of the virus by the human response. Significantly, if rubeola virus were present in the gut, as suggested by photomicrographs by Wakefield, such virus particles would be protected from the body's immune defenses because antibodies do not generally travel from the circulatory system to the lumen of the intestinal tract. Accordingly, massive numbers of circulating antibodies may be of no real protective value against rubeola virus in the gut.

While the possibility of a link between MMR vaccination and autism has prompted suggestions that measles vaccine be applied singly rather than as a component of a multi-component vaccine as a means for reducing the incidence of autism there remains a need for method of treating the symptoms of autism in subjects who already affected by the condition.

Multiple sclerosis (MS) is a slowly progressing demyelinating disease of the central nervous system which is insidious and characterized by multiple and varied neurological symptoms characterized by remissions and exacerbations. The onset of the disease usually occurs between 20 and 50 years of age with a peak occurring in people 30 years old. MS is believed to be immunological in nature but treatment with immuno-suppressive agents is not advised. The prevalence of MS varies widely with location with the highest prevalence found at higher latitudes in the northern Europe and northern North America. The geographic variation suggests that MS may in part be caused the action of some environmental factor that is more common at high latitudes. The prevalence of MS in some ethnic groups and its low incidence and near absence in other ethnic groups suggests a genetic influence on susceptibility. Twins studies and other familial studies confirm that susceptibility to MS is at least partly genetic. While the genetic factors that confer susceptibility to MS are only partly known the human leukocyte antigen (HLA) class II DRB1*1501 haplotype has been found to be reproducibly associated with MS.

The evidence for MS being an autoimmune or an immune-mediated disease includes the pathologic findings of plaques in the myelinated fibers, an increased synthesis of IgG in the cerebrospinal fluid, and various abnormalities of leukocyte function. The autoimmune response could be either the primary cause of the disease of an epiphenomenon of other disease processes. According to one theory, an autoimmune attack on myelin is precipitated by an infectious organism that contains a protein similar to a myelin protein. Infection by the organism then elicits a vigorous immune response from lymphocytes that recognize the cross-reactive protein and thereby also attack the myelin.

Treatment of MS can be classified in terms of treatment of acute relapses, the prevention or relapses and the management of symptoms. Acute relapses are typically treated with oral prednisone and with dexamethasone while interferon beta has shown potentially promising results in the prevention of relapse. Glatiramer which is a synthetic random polymer of four amino acids also shows promise in reducing the frequency of relapses in MS. While its mechanism is not definitively established it is believed that it binds to MHC class II antigen and induces organ-specific T helper 2 cell responses. Many symptoms of MS such as depression, fatigue, spasticity, bladder dysfunction and pain are treated by conventional means. Of interest to the present invention are the disclosures of McMichael U.S. Pat. No. 4,521,405 which discloses a method for alleviating the symptoms of multiple sclerosis comprising the administration of inactivated attenuated measles virus. Nevertheless, despite the known therapies there remains a desire in the art for new and improved methods for treatment of multiple sclerosis.

SUMMARY OF THE INVENTION

The present invention is directed to methods for the treatment of symptoms of CNS and behavioral disorders selected from the group consisting of autism multiple sclersosis, attention deficit disorder (ADD) and attention deficit hyperactivity disorder (ADHD). In particular, the invention relates to the discovery that symptoms of these disease states may be treated by administration of anti-rubeola (anti-measles) antibodies. Without intending to be bound by a particular theory of the invention it is believed that administration of anti-rubeola antibodies may be effective to neutralize live rubeola virus in the gut or elsewhere and thereby alleviate symptoms associated with the presence of rubeola virus.

Specifically, the invention provides a method of treating the symptoms of autism comprising the step of administering an effective amount of anti-rubeola antibody. The invention also provides a pharmaceutical composition for administration to a subject for treatment of autism comprising anti-rubeola antibody in an amount effective to alleviate one or more symptoms of autism related to language ability, bowel function, attitude and sleep. It is contemplated that the anti-rubeola antibody may be human or derived from other animal species and may be polyvalent or monoclonal. According to one aspect of the invention the antibody is a rabbit polyvalent antibody.

The invention also provides a method of treating the symptoms of multiple sclerosis comprising the step of administering an amount of anti-rubeola antibody effective to treat one or more symptoms of multiple sclerosis including numbness, fatigue, muscle control and the like.

The invention further provides a method of treating the symptoms of attention deficit disorder (ADD) and attention deficit hyperactivity disorder (ADHD) comprising the step of administering an amount of anti-rubeola antibody effective to treat one or more symptoms of ADD or ADHD such as anxiety or hyperactivity.

While it is contemplated that anti-rubeola antibody may be effectively administered in a variety of manners as would be apparent to those of skill in the art it is particularly preferred that the anti-rubeola virus be administered enterically and preferably orally. Preferred methods for oral administration include by oral drench or alternatively and in an enterically protected form. Suitable dosages can be determined empirically by those of skill in the art depending upon the route of administration and the body weight of the child. Nevertheless, when the anti-rubeola antibodies are administered by oral drench a dosage greater than 0.01 mg is preferred with a dosage in the range of from 0.1 mg to 10 mg antibody per dose being more preferred and a dosage of about 1 mg of antibody being particularly preferred. Dosages of anti-rubeola antibodies may be administered multiple times per day but a preferred protocol for treatment according to the invention comprises one dosage daily of 1 mg anti-rubeola antibody for three consecutive days.

DETAILED DESCRIPTION OF THE INVENTION

The present invention provides methods for the treatment of symptoms of autism through the administration of effective amounts of anti-rubeola antibodies to patients suffering from autism. The invention also provides pharmaceutical compositions for administration to a subject for treatment of autism comprising anti-rubeola antibody in an amount effective to alleviate one or more symptoms of autism.

The invention described herein provides methods for treating ADD/ADHD, autism, MS and related disorders. The invention describes the use of specific anti-rubeola antibody used at relatively high concentrations as a drench, and at a relatively low dose as a systemic signal to specifically inhibit virus replication or the body's aberrant response to the virus that results in the symptoms characteristic of the diseases.

Successful treatment of several CNS or behavioral disorders can be accomplished by low or high dose therapy using rubeola-specific antibody. According to one method of the invention, one cc of saline or other appropriate carrier containing 1 mg of anti-rubeola virus antibody is used as a drench to inactivate virus in the patient's gut. The 1 cc is administered orally by mixing with a small volume of water or juice and swallowed, or by squirting into the back of the mouth via syringe.

According to an alternative method of the invention, anti-rubeola antibody can be administered via sublingual drop wherein each drop equals one dose and contains approximately $8 \times 10^{-5}$ mg of anti-rubeola antibody. This dose can vary according to specific titration on a patient-by-patient basis from $1 \times 10^{-10}$ to a $1 \times 10^{-2}$ mg/drop.

Anti-rubeola antibody useful in practice of the invention may be obtained from a variety of sources. Suitable antibodies may be polyclonal or monoclonal and can be derived from various animal sources. A preferred anti-rubeola antibody for use in practice of the invention is polyvalent rabbit anti-rubeola antibody available from Cortex Biochemicals, San Leandro, Calif.

Provided below is a description of case histories of four patients whose symptoms of autism were treated according to practice of the invention which provide evidence of the effectiveness of the treatment methods described herein. The following examples are intended to illustrate practice of the preferred embodiments of the invention but should not be considered as limiting. Numerous additional embodiments and improvements are apparent to those of ordinary skill in the art upon consideration of the Examples.

The invention described herein provides methods for treating patients with central nervous system or behavioral disorders by the administration of anti-rubeola virus antibody. The target of the therapy is to eliminate infecting virus, reduce virus load, or negate the body's aberrant immune response directed against the virus or an antigenically closely related target.

EXAMPLE I

According to this example, an eight year old autistic male was treated by administration of 1 mg of polyvalent rabbit anti-rubeola antibody (Cortex Biochemicals, San Leandro, Calif.) in 1 mL saline by oral drench. The dosage was repeated once daily for a total of three consecutive days. After the third dose, he showed marked improvement in spontaneous language, echolalia and attitude. For the first time in his life he commented on things he was doing. His sleep improved, as did his interest in people and his surroundings. When switched to sublingual drops of a lower concentration of antibody, he continued to improve over a four month period.

EXAMPLE II

According to this example, a seven year old autistic male was treated by administration of 1 mg of polyvalent rabbit anti-rubeola antibody (Cortex Biochemicals, San Leandro, Calif.) in 1 mL saline via oral drench for three consecutive days. The patient showed significant improvements in sleep, bowel function, verbals, eye contact and attitude. His tutors reported that "Every day is his best ever." After about six weeks without further therapy, he was treated with a daily oral drench of antibody at a lower concentration (0.1 mg/dose) for one week. There was a reversal in all gains noted above. Exaggerated autistic symptoms were noted. He appeared to be sick, had no interest in others or in his immediate environment, and appeared to be "spacey." His condition improved rapidly when again drenched with the higher concentration (1 mg/dose) antibody. This patient was then given sublingual antibody in low concentration at the rate of one drop every other day. Patient demonstrated improved bowel function, sleep, attentiveness and interest and decreased hyperactivity. He continues to do well on the sublingual drop.

EXAMPLE III

According to this example, a five year old autistic boy was treated by administration of concentrated (1 mg/cc) polyvalent rabbit anti-rubeola antibody (Cortex Biochemicals, San Leandro, Calif.) in 1 mL saline for three consecutive days using an oral drench. There was a transient (4 day) increase in autistic characteristics followed by significantly improved verbalization, better use of language, body movements that were more mature and less infantile, and improved eye contact and independent playing. Daily administration of a lower dose (0.1 mg) by drench lead to some improvement (verbal, receptive language, hyperactivity) followed by broad spectrum decline. As in Example II, the decline was reversed with re-introduction of drench at 1 mg/dose. It is to be noted that this patient's worsening was pronounced, to the point that his parent felt he had reverted to his condition at age one. He has recovered with the original drench and continues to show steady improvement.

EXAMPLE IV

An eleven year old autistic male received three doses of the concentrated drench (1 mg anti-rubeola antibody per dose) on three consecutive days. After the first dose, and continuing for at least two weeks, he showed improved cognition, verbalization, sleep patterns and attitude. He then became "spacey," was constipated, had inappropriate mood swings and experienced unexplained bouts of crying. When treated with the lower concentration of antibody administered by sublingual drop, his attitude improved, he had transient diarrhea followed by normal stools, better days at school and a voracious appetite. This patient continues to use sublingual drops, but the dose per day is not constant. While on some days he does well with the $8\times10^{-5}$ mg concentration of antibody, other days he does best with a concentration several times greater or lesser than this standard.

EXAMPLE V

According to this example, a 40+ year old female with progressing multiple sclerosis of long standing was treated with three consecutive daily drenches of polyvalent rabbit anti-rubeola antibody (Cortex Biochemicals, San Leandro, Calif.) in 1 mL saline (1 mg/dose). After the first dose, she experienced improvement of her condition relative to several parameters. There was a decrease in hand numbness for the first time in years, she could lift her legs slightly, had decreased leg numbness, improved vision, decreased fatigue, improved bladder control and improved balance. After two months, she could write without difficulty, had her first spontaneous bowel movement in several years and greater energy. When switched to sublingual drop therapy with one or two drops daily, she showed further improvement in balance, decreased leg tightness, completely normal hand function, increased tolerance to a broad spectrum of foods. No negative effects were noted. She continues daily sublingual drop therapy after nearly three months.

EXAMPLE VI

According to this example, a 48 year old multiple sclerosis patient was treated with three consecutive daily drenches of polyvalent rabbit anti-rubeola antibody (Cortex Biochemicals, San Leandro, Calif.) in 1 mL saline (1 mg/dose). After three days, he showed better bowel and bladder function and control, decreased foot numbness, better balance and walking. These improvements have been maintained with sublingual drop therapy using one drop (1 mg/dose) daily.

EXAMPLE VII

According to this example, a ten year old male with ADD/ADHD was treated with three consecutive daily drenches of polyvalent rabbit anti-rubeola antibody (Cortex Biochemicals, San Leandro, Calif.) in 1 mL saline (1 mg/dose). He showed nearly immediate calming which persisted without additional treatment for approximately four weeks.

It is anticipated that numerous variations and modifications of the embodiments of the invention described above will occur to those of ordinary skill in the art when apprized of the teachings of the present specification. Accordingly, only such limitations as appear in the appended claims should be placed thereon.

What is claimed:

1. A method of treating the symptoms of autism comprising the step of administering an effective amount of anti-rubeola antibody.

2. The method of claim 1 wherein said anti-rubeola antibody is a monoclonal antibody.

3. The method of claim 1 wherein said anti-rubeola antibody is administered orally.

4. The method of claim 3 wherein said anti-rubeola antibody is administered by oral drench.

5. The method of claim 3 wherein said anti-rubeola antibody is administered sublingually.

6. The method of claim 3 wherein said anti-rubeola antibody is administered in an enterically protected form.

7. The method of claim 1 wherein said anti-rubeola antibody is administered at a dosage of from 0.1 mg to 10 mg per dose.

8. A method of treating the symptoms of multiple sclerosis comprising the step of administering an effective amount of anti-rubeola antibody.

9. The method of claim 8 wherein said anti-rubeola antibody is a monoclonal antibody.

10. The method of claim 8 wherein said anti-rubeola antibody is administered orally.

11. The method of claim 10 wherein said anti-rubeola antibody is administered by oral drench.

12. The method of claim 10 wherein said anti-rubeola antibody is administered sublingually.

13. The method of claim 10 wherein said anti-rubeola antibody is administered in an enterically protected form.

14. The method of claim 8 wherein said anti-rubeola antibody is administered at a dosage of from 0.1 mg to 10 mg per dose.

15. A method of treating the symptoms of a disease state selected from the group consisting of attention deficit disorder (ADD) and attention deficit hyperactivity disorder (ADHD) comprising the step of administering an effective amount of anti-rubeola antibody.

16. The method of claim 15 wherein said anti-rubeola antibody is a monoclonal antibody.

17. The method of claim 15 wherein said anti-rubeola antibody is administered orally.

18. The method of claim 17 wherein said anti-rubeola antibody is administered by oral drench.

19. The method of claim 17 wherein said anti-rubeola antibody is administered sublingually.

20. The method of claim 17 wherein said anti-rubeola antibody is administered in an enterically protected form.

21. The method of claim 15 wherein said anti-rubeola antibody is administered at a dosage of from 0.1 mg to 10 mg per dose.

22. A dosage unit of pharmaceutical composition for administration to a subject for treatment of a disease state selected from the group consisting of autism, multiple sclerosis, attention deficit disorder (ADD) and attention deficit hyperactivity disorder (ADHD) comprising anti-rubeola antibody in an amount effective to alleviate one or more symptoms of a disease state selected from the group consisting of autism, multiple sclerosis, attention deficit disorder (ADD) and attention deficit hyperactivity disorder (ADHD);

wherein said amount of anti-rubeola antibody is a single dose between 0.1 mg and 10 mg.

* * * * *